(12) United States Patent
Boehlke et al.

(10) Patent No.: US 6,500,845 B1
(45) Date of Patent: Dec. 31, 2002

(54) LACTAM DERIVATIVES AS IMMUNOMODULATING AGENTS

(75) Inventors: Horst Boehlke, Stolberg (DE); Michael Finkam, Aachen (DE); Oswald Zimmer, Wuerselen (DE); Johannes Schneider, Stolberg (DE); Stephan Wnendt, Aachen (DE); Kai Zwingenberger, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 08/471,198

(22) Filed: Jun. 6, 1995

(30) Foreign Application Priority Data

Jun. 24, 1994 (DE) .......................................... 44 22 237

(51) Int. Cl.$^7$ ................. A61K 31/4523; C07D 417/04; C07D 401/04
(52) U.S. Cl. ....................... 514/321; 546/198; 546/200; 514/323
(58) Field of Search ................. 546/198, 200; 514/321, 323

(56) References Cited

U.S. PATENT DOCUMENTS

| | | | | |
|---|---|---|---|---|
| 4,399,145 A | * | 8/1983 | Graudums et al. .......... | 514/321 |
| 5,008,394 A | | 4/1991 | Guenther et al. | |
| 5,382,514 A | * | 1/1995 | Passaniti et al. ........... | 435/7.21 |
| 5,593,990 A | * | 1/1997 | D'Amato ................. | 514/235.2 |

FOREIGN PATENT DOCUMENTS

| WO | WO 92/14455 | 9/1992 |
|---|---|---|
| WO | WO 94/20085 | 9/1994 |
| WO | WO94/20085 | * 9/1994 |

OTHER PUBLICATIONS

J. March, Advanced Organic Chemistry: Reactions, Mechanisms, and Structure, 4th ed., 1992, John Wiley & Sons, Inc., pp. 1209–1211.*

Helm, F.C. et al Arzneim. –Forsch. 1981, 31(6), pp. 941–949.*
March, J. Advanced Organic Chemistry, 1992, John Wiley adn Sons Inc. pp. 442, 443, and 910–912.*
Chemical Abstracts, vol. 113. No. 3, Jul. 16, 1990, Columbus Ohio, Abstract No. 17466f.
Chemical Abstracts, vol. 112, No. 1, Jan. 1, 1990, Columbus Ohio, Abstract No. 7314v.
Chemical Abstracts, vol. 107. No. 11, Sep. 14, 1987, Columbus Ohio, Abstract No. 96568t.
Joensson et al., "Chemical Structure and Teratogenic Properties", Acta Pharmaceutica Suecia, vol. 9, pp. 431–446 (1972).
S.H. Lim, "Successful Treatment With Thalidomide of Acute Graft–Versus–Host Disease After Bone–Marrow Transplantation", The Lancet, 1988, p. 117.
G.L. Fite, "The Vascular Lesions of Leprosy", International Journal of Leprosy, vol. 9, pp. 193–201 (1994).
Vogelsang, Georgia B., "Thalidomide for the Treatment of Chronic Graft–Versus–Host Disease", The New England Journal of Medicine, vol. 326, pp. 1055–1058 (1992).
Ochonisky, Sophie, "Thalidomide Use in Dermatology", European Journal of Dermatology, vol. 4, pp. 9–15 (1994).

* cited by examiner

Primary Examiner—Charanjit S. Aulakh
Assistant Examiner—Goya N. Duckett
(74) Attorney, Agent, or Firm—Crowell & Moring LLP

(57) ABSTRACT

The invention relates to the use of certain lactam derivatives corresponding to the formula I

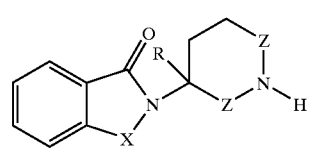

as pharmaceutical compounds with immunomodulatory activity, to new lactam derivatives, and to processes for preparing these derivatives.

13 Claims, No Drawings

LACTAM DERIVATIVES AS IMMUNOMODULATING AGENTS

This invention concerns the use of lactam derivatives as pharmaceutical compounds, new lactam derivatives as well as processes for their preparation.

Excessive formation of cytokines such as tumor necrosis factor a (TNF-α), interleukin-2 (IL-2) and γ-interferon (IFN-γ), are pivotal in the pathogenesis of the Graft-versus-Host-Syndrome, transplant rejection and other immunologically triggered diseases such as Morbus Behcet, aphthous stomatitis, erythema nodosum leprosum, Morbus Boeck, cutaneous lupus erythematodes and rheumatoid arthritis. Modulation of cytokine release, e. g. using cyclosporin A or glucocorticoids, is a therapeutical option in these pathological situations. The problem of therapy by immunosuppressants, however, is that blockade of the immune system entails opportunistic infections, e.g. by fungi or viruses. Therefore, compounds which only partly suppress cellular immune reactions promise improvements of therapy. At present, no satisfactory compounds are available for this purpose. Thus, there has remained a need for further immunomodulating substances.

Thalidomide has been used since the late 1960's in the treatment of erythema nodosum leprosum and several other disease entities such as Morbus Behcet, Lupus erythematodes, stomatitis aphthosa and Graft-versus-Host-Syndrome [*The Lancet* 1988, 117; *N. Engl. J. Med.* 326, 1055 (1992); *Eur. J. Dermatol.* 4, 9 (1994)]. During treatment with thalidomide there is no impairment of immunocompetence, and during all these years no association of thalidomide therapy with opportunistic infections has been reported. These findings correspond to experimental data where thalidomide, in contrast to typical immunosuppressants, does not reduce the release of cytokines TNF-α, IL-2 and IFN-γ below detection limits. Furthermore, and also in contrast to cyclosporin A and dexamethasone, thalidomide has not been reported to inhibit the proliferation of immunocompetent lymphocytes.

It has now been found that certain lactam derivatives have similar or superior activity compared to thalidomide in certain pharmacological models while not being teratogenic.

Accordingly, the present invention relates to the use of a lactam derivative of formula I

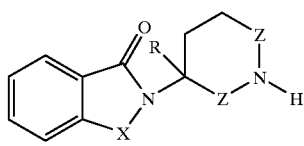

in which X is CH$_2$, S or Se and R is a C$_{1-6}$-alkyl or the benzyl group and wherein Z and Z' are different and denote CH$_2$ or CO or Z and Z' are both CO, in racemic or optically active form as a pharmaceutical agent.

The lactam derivatives of formula I, in particular those lactam derivatives of formula I in which R is a C$_{1-3}$-alkyl group, i.e. a methyl-, ethyl-, propyl- or isopropyl group, are broadly immunomodulatory, especially immunosuppressive. Therefore the lactam derivatives of formula I are preferably used as immunomodulatory and/or immunosuppressive therapeutic agents.

Furthermore, lactam derivatives of formula I are especially suitable to reduce neoangiogenesis. Neoangiogenesis, i.e. the pathological formation of new blood vessels, is an undesirable reaction associated with immunological diseases such as Morbus Crohn and infections with mycobacterium leprae [*Int. J. Leprosy* 9, 193 (1941)] and granulomatous diseases.

In order to treat diseases of the immune system, such as Graft-versus-Host-disease, graft rejection, Morbus Behcet, Lupus erythematodes, autoimmune consequences of chronic infections, Morbus Crohn or Kawasaki syndrome lactam derivatives of formula I may be administered orally, intravenously, intraperitoneally, intradermally or intramuscularly, intranasally as well as topically, e.g. in the case of infections of the skin, the mucous membranes or the eyes. The amount dispensed to patients varies according to the weight of these patients and the route of administration, the indication and the severity of disease. Usually 1 to 10 mg/kg of a lactam derivative of formula I are administered.

Examples of suitable preparations for oral administration include tablets, sugar-coated tablets, capsules, granulates, drops, syrups and suspensions, for parenteral, topical or inhalatory administration solutions, suspensions, easily reconstituted dry preparations as well as sprays. Lactam derivatives of formula I may also be administered cutaneously in a depot in soluble form or by a patch, if necessary with additives that enhance penetration through the skin. Orally or cutaneously administerable formulations of these lactam derivatives can have the property of prolonged or sustained release.

All the above-mentioned types of pharmaceutical preparations are known per se and, since the lactam compounds according to the invention are chemically stable, incorporating them into these formulations is within the skill of a skilled pharmaceutical chemist. In the preparation of pharmaceuticals the appropriate care must be taken when choosing excipients, e.g. vehicles, fillers, solvents, diluents, coloring agents, flavoring agents, binders and disintegrants, and, in particular when preparing parenterally administrable preparations stability and isotonicity of liquid formulations has to be ensured.

Further the present invention relates to hitherto unknown lactam derivatives of formula I

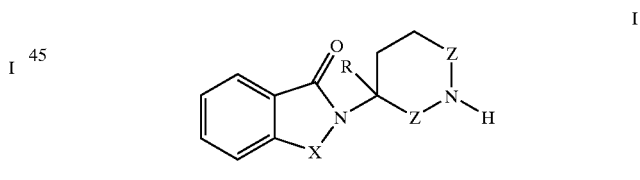

wherein X is CH$_2$, S, or Se and R is a C$_{1-6}$-alkyl- or the benzyl group, Z and Z' are different and denote CH$_2$ or CO, or Z and Z' are both CO with the proviso, that X is not S, when Z is CO and Z' is CH$_2$, in racemic or in optically active form.

The compounds of formula I according to the invention show configurational stability. Compounds of formula I in which R is a methyl, ethyl, propyl or isopropyl group are preferred.

Depending on the meaning of the variable X, different methods have to be used to prepare the lactam derivatives of formula I. The subject matter of the invention therefore also includes several processes for preparing the lactam compounds according to the invention.

One aspect of the invention is a process for preparing a lactam derivative of formula I

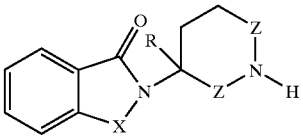

I wherein X is CH$_2$ and R is a C$_{1-6}$-alkyl group or the benzyl group, Z and Z' are different and denote CH$_2$ or CO, or Z and Z' are both CO, characterized in that a compound of formula II

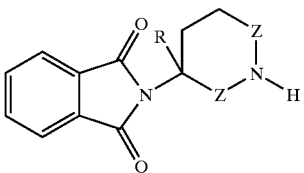

II is reduced with zinc, lithium aluminum hydride or a complex borohydride at a temperature between +20° C. and +100° C.

Preferably the reaction is performed in a solvent. Suitable solvents include aliphatic carboxylic acids with 1 to 6 carbon atoms, for example formic acid, ethanoic acid, propanoic acid, butanoic acid, pentanoic acid, hexanoic acid, or mixtures of these acids, and/or aliphatic ethers, for example diethyl ether, diisopropyl ether, tetrahydrofuran, dioxane, or mixtures of such ethers.

Examples of suitable complex borohydrides include the borane/tetrahydrofuran complex, lithium triethyl borohydride and lithium diisopropylamino borohydride.

Compounds of formula II can be obtained in a known manner by reaction of compounds of formula V

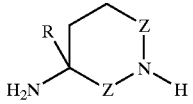

V with phthalic anhydrides, followed by an oxidation reaction.

The invention also relates to a process for preparing a lactam derivative of formula I

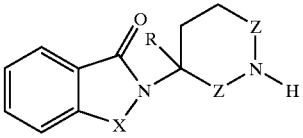

I wherein X is CH$_2$ and R is a C$_{1-6}$-alkyl group or the benzyl group, Z and Z' are different and denote CH$_2$ or CO, or Z and Z' are both CO, characterized in that a compound of formula

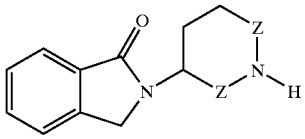

III is reacted with a basic compound and subsequently with a C$_{1-6}$-alkyl halide or a benzyl halide.

The reaction of a compound of formula III, which compounds are accessible via a method described in *Acta Pharmaceutica Suecica* 9, 431 (1972), with a basic compound, for example methyllithium, butyllithium, 1,1,1,3,3,3-hexamethyl disilazane, lithium diisopropylamide, or an alkali alcoholate, is preferably performed in anhydrous solvents, especially in aliphatic or cyclic ethers, for example diethyl ether, diisopropyl ether, tetrahydrofuran, and/or dioxane at a temperature between −78° C. and 0° C. The following alkylation with a C$_{1-6}$-alkyl halide or a benzyl halide, especially with a C$_{1-3}$-alkyl chloride, -bromide, or -iodide is preferably performed at temperatures between −30° C. and +20° C.

The invention additionally relates to a process for preparing a lactam derivative of formula I

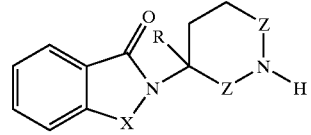

I wherein X is S or Se, and R is a C$_{1-6}$-alkyl group or the benzyl group, Z and Z' are different and denote CH$_2$ or CO, or Z and Z' are both CO, with the proviso, that X is not S, when Z is CO and Z' is CH$_2$, characterized in that a compound of formula IV

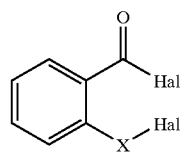

IV wherein Hal and Hal' have the same or different meanings and represent a chlorine or bromine atom, is reacted with a compound of formula V

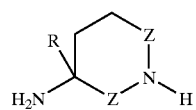

V in the presence of a base at a temperature between −20° C. and +50° C.

Preferably a compound of formula IV in which Hal and Hal' represent chlorine atoms is reacted in the presence of a solvent, for example N,N-dimethylformamide, and a base, for example triethylamine, pyridine and/or diisopropyl ethyl amine. Compounds of formula IV can be prepared by a process described in published European Patent Application Nos. EP 54,672 and EP 354,412.

Compounds of formula VI

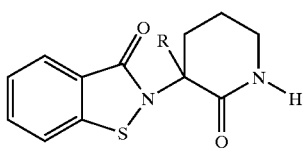

are accessible via a process which is described in EP 54,672.

EXAMPLES

The ratio of the components of solvent mixtures is given in volume/volume.

Example 1

2-(3-Methyl-2-oxo-piperidin-3-yl)-benzo[d]isoselenazol-3-one

To a solution of 0.47 g of 3-amino-3-methyl-piperidin-2-one in 10 ml of N,N-dimethylformamide were added dropwise, while stirring at −20° C., first a solution of 0.93 g of 2-chloroseleno-benzoyl chloride in 5 ml of N,N-dimethylformamide and then 1 ml of triethylamine. The mixture was stirred for 22 hours at −20° C. and then 5 ml of water were added dropwise. The crystalline precipitate was filtered out with suction and recrystallized from 20 ml of a 3:5 mixture of ethyl alcohol and ethyl acetate to give 0.49 g (43.4%) of 2-(3-methyl-2-oxo-piperidin-3-yl)-benzo[d]isoselenazol-3-one in form of white crystals, melting between 263° C. and 270° C.

1H-NMR (DMSO-d6): 1.72 (s, 3H, $CH_3$); 1.70–1.90 (m, 3H, $CH_2$, CH); 2.44–2.55 (m, 1H, CH); 3.17–3.34 (m, 1H, $CH_2$); 7.38–8.04 (m, 5H, $CH_{ar}$, NH) ppm.

Example 2

3-Methyl-3-(1-oxo-1,3-dihydro-isoindol-2-yl)-piperidine-2,6-dione

Method of Preparation A

To a solution of 1.7 ml of diisopropylamine in 50 ml of absolute tetrahydrofuran were added dropwise, while stirring at 10° C. to 15° C. under an atmosphere of dry nitrogen, 13.1 ml of n-butyllithium solution (15% in n-hexane). After stirring for 40 minutes, 1.95 g of triturated 3-(1-oxo-1,3-dihydro-isoindol-2-yl)-piperidine-2,6-dione were added in small portions. In doing so, a yellow-orange suspension was formed. The mixture was stirred for a further 60 minutes. Then 1.25 ml of iodomethane were added dropwise and stirring was continued for another 60 minutes.

In order to work up the reaction mixture, first 35 ml of hydrochloric acid (1 mole/liter) were added, then the mixture was diluted with 50 ml of tetrahydrofuran and 100 ml of diethyl ether. The aqueous layer was separated, the organic layer was washed with 30 ml of a diluted aqueous solution of sodium hydrogencarbonate, dried over anhydrous magnesium sulfate and evaporated in vacuo. To remove unconverted starting material, the residue was extracted twice with 10 ml portions of boiling tetrahydrofuran, and once with 5 ml of tetrahydrofuran at 20° C. Purification of the residue by HPLC (mobile phase: methanol/water=20/80; stationary phase: 10 m RP 18 Nucleosil) yielded 0.33 g (16%) of 3-methyl-3-(1-oxo-1,3-dihydro-isoindol-2-yl)-piperidine-2,6-dione in form of white crystals, having a melting point of 231–232° C.

1H-NMR (DMSO-d6): 1.69 (s, 3H, $CH_3$); 1.86–1.96 (m, 1H, $CH_2$); 2.49–2.64 (m, 1H, $CH_2$); 2.68–2.80 (m, 2H, $CH_2$—CO); 4.64, 4.70 (2d, 2H, $CH_2$—N); 7.49–7.51 (m, 1H, $CH_{ar}$); 7.61–7.65 (m, 3H, $CH_{ar}$); 10.88 (s, 1H, NH) ppm.

Method of Preparation B 8.2 g of 2-(3-methyl-2,6-dioxo-piperidin-3-yl)-isoindole-1,3-dione were dissolved in 470 ml of glacial acetic acid. When the solution was boiling under reflux, five 3.9 g portions of zinc dust were added at intervals of one hour. Then zinc was removed by filtration and washed with 1,4-dioxane. The filtrate was evaporated under vacuo yielding a crude product which was crystallized from ethyl alcohol. The residue obtained by evaporation of the mother liquor was purified by column chromatography (stationary phase: silica gel 60, MERCK, 40–63 mm; mobile phase: 4:1 acetone/dichloromethane). Thus 2.7 g (35%) of 3-methyl-3-(1-oxo-1,3-dihydro-isoindol-2-yl)-piperidine-2,6-dione were obtained.

Example 3

(+)-3-Methyl-3-(1-oxo-1,3-dihydro-isoindol-2-yl)-piperidine-2,6-dione and (−)-3-Methyl-3-(1-oxo-1,3-dihydro-isoindol-2-yl)-piperidine-2,6-dione Separation of the racemate of Example 2 by HPLC using tribenzoylcellulose as a chiral stationary phase (mobile phase: 95:5 methanol/water) gave the two enantiomers in the form of white crystals melting at from 253° C. to 255° C.

Example 4

2-(3-methyl-2-oxo-piperidin-3-yl)-benzo[d]isothiazol-3-one

This lactam derivative was synthesized by reaction of 3-amino-3-methyl-piperidin-2-one with 2-chloromercapto-benzoylchloride using the procedure described in Example 10 of EP 54,672.

Pharmacological Studies

Effectiveness of the Lactam Derivatives According to the Invention in Animal Experimentation.

In order to characterize the in vivo immunopharmacological effects of lactam derivatives of formula I, a test model was chosen in which T-lymphocytes are stimulated. The relevance of the immunopharmacological test model, in which the T-cell is one of the target cells, is indicated by the central role of the T-cell in diverse immunological diseases. These diseases include Graft-versus-Host-Disease (GvHD), graft rejection (Host-versus-Graft), autoimmune diseases such as late infection reaction (e.g. rheumatoid fever, rheumatoid arthritis), Behcet's disease (mucocutaneous ulcerations) and Kawasaki's disease (multisystem vasculitis).

Stimulation of T-cells was achieved by i.v.-administration of the staphylococcal enterotoxin B (SEB; 200 μg) in galactosamine-pretreated Balb/c mice. SEB belongs to the group of superantigens, which in association with the MHC-II-complex (major histocompatibility complex, class II) of an antigen-presenting cell induces activation of the T-cell receptor (TCR). As a measure of T-cell activation serum concentrations of the cytokine IL-2 were determined. IL-2 is generated by $T_{H1}$-cells. Serum IL-2 was determined using a commercial ELISA-test, which is specific for murine IL-2. Injection of SEB induced a time-dependent increase of serum IL-2 levels with a clear maximum at 2 hours after SEB-administration. The origin from T-cells of IL-2 as determined in serum was verified by the fact that T-cell deficient SCID-mice in contrast to Balb/c mice did not generate any IL-2 upon injection of the same dose of SEB.

The compounds according to the invention were dissolved in an aqueous 1% carboxymethyl cellulose solution (1% CMC) and administered intraperitoneally in dosages of 10–400 mg/kg and in a volume of 1 ml/kg 30 minutes before SEB-injection. Animals of the control group received 1 ml/kg vehicle solution (16% CMC) intraperitoneally at the same time. Serum IL-2 concentrations were determined 2 hours after SEB-administration (i.e. 2.5 hours after administration of the compounds). Table 1 shows the maximum inhibitory effects (in %) of serum IL-2 levels in the groups treated with a lactam derivative compared to the control group. The percentage values are given as mean values with standard error of the mean of n=6–8 single experiments each. The dosages reducing serum IL-2 concentrations by 40% ($ED_{40}$-values) were calculated by means of a regression line.

TABLE 1

Effect of lactam derivatives of formula I on IL-2 release in vivo.

| Lactam Derivative prepared according to Example No. | Maximum inhibition of serum IL-2 increase in % (dose in parentheses) | $ED_{40}$ [mg/kg i.p.] |
|---|---|---|
| Example 2 | 56 ± 3 (200 mg/kg) | 112 |
| Example 3 (−) enantiomer | 54 ± 5 (400 mg/kg) | 297 |
| Example 1 | 43 ± 5 (10 mg/kg) | ca. 20 |
| Example 4 | 52 ± 3 (10 mg/kg) | <10 |
| Thalidomide (reference) | 56 ± 10 (400 mg/kg) | 171 |

Comparative investigations showed that the lactam derivatives according to the invention, in contrast to glucocorticoids, inhibited T-cell activity also when they were administered 30 minutes before T-cell stimulation by SEB. An inhibitory effect of glucocorticoids, however, was only possible when these compounds were administered 18 hours before T-cell stimulation.

Effectiveness of Lactam Derivatives According to the Invention on Human Cells in Vitro.

The release of cytokines from human mononuclear cells of the peripheral blood, i.e. T-cells, B-cells and monocytes, can be studied in vitro after stimulation by lipopolysaccharide (LPS) or the toxic shock syndrome toxin-1 (TSST-1). LPS is a component of the bacterial cell wall and stimulates monocytes and macrophages. TSST-1 is a bacterial superantigen that stimulates T-cells as well as monocytes/ macrophages. Superantigens bind to the Vβ chain of the T-cell receptor and to the MHC class II and thus simulate the recognition by a specific T-cell receptor of an antigen presented by the MHC class II. Activation of cells by LPS or TSST-1 induces the release of TNF-α, IFN-γ and other cytokines.

Mononuclear cells were prepared from the heparinized blood of at least three voluntary donors. For this purpose, 20 ml blood samples each were separated according to well known procedures using a Ficoll-Paque gradient. The cells were harvested and washed three times with a cell culture medium. This cell culture medium was composed of RPMI 1640 medium supplemented with 2 mM of glutamine (Life Technologies, Eggenstein, Germany), 10% fetal calf serum (Life Technologies), 50 $\mu$g/ml of streptomycin (Sigma, Deisenhofen, Germany), 50 IU/ml of penicillin (Sigma) and 100 $\mu$M of b-mercaptoethanol (Merck, Darmstadt, Germany). The mononuclear cells were suspended in 15 ml of cell culture medium and separated in 1 ml fractions in sterile 24-well incubation plates (Sigma). 1 $\mu$l of dimethylsulfoxide (DMSO) or 1 $\mu$l of a DMSO-solution containing 5 ' by weight of a compound according to the invention was added to each of the 1 ml fractions. After incubation for 1 hour in a $CO_2$-incubator (5% $CO_2$, 90% humidity), 2.5 $\mu$g of LPS (from E. coli 0127: B8, Sigma) or 0.1 $\mu$g of TSST-1 (Sigma) were added to each of the fractions containing a compound according to the invention. Incubation of the cultures was continued for 20 hours. The concentrations of TNF-α and IFN-γ in the cell culture supernatants were determined with commercial ELISA-tests (Boehringer Mannheim, Germany; Endogen, Boston, Mass.).

Table 2 shows the effects of the lactam derivatives according to the invention and of thalidomide on LPS-induced TFN-α release. The $IC_{50}$ value is the concentration in $\mu$g/ml which produces a 50% inhibition in the release of TFN-α. Lactam compouds according to the invention inhibited TFN-α release more potently than thalidomide did.

TABLE 2

Inhibition of TNF-α release and $IC_{50}$-values of lactam derivatives of formula I.

| Lactam derivative prepared according to Example No. | Inhibition of TNF-α release in (%) at a concentration of 50 $\mu$/ml | $IC_{50}$ [$\mu$g/ml] |
|---|---|---|
| Example 2 | 72 ± 8 | 10 |
| Example 3 (−) enantiomer | 82 ± 5 | 8 |
| Example 1 | 93 ± 1 | not determined |
| Example 4 | 93 ± 9 | not determined |
| Thalidomide (reference) | 54 ± 7 | 50 |

The effect of the lactam derivative prepared according to Example 2 on the TSST-1-induced release of TNF-α and IFN-γ is enhanced compared to thalidomide.

The results of the in vivo and in vitro investigations demonstrate that the compounds according to the invention are able to inhibit the activation of immunocompetent cells. Release of the cytokines IL-2, TNF-α and IFN-γ were used as a measure of cell activation. The attenuating effect of the compounds according to the invention on the release of these cytokines, which are specific for cell activation, indicates that these compounds are suitable for treating diseases which are associated with hyperreactivity of immunocompetent cells. For purpose of such treatments, the lactam derivatives of formula I can be administered prophylactically as well as curatively.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of treating a condition selected from the group consisting of Graft-versus-Host-Syndrome, transplant or graft rejection, Morbus Behcet, erythema nodosum leprosum, Morbus Boeck, rheumatoid fever, rheumatoid arthritis, lupus erythematodes, stomatitis aphthosa, autoimmune consequences of chronic infections, Morbus Crohn, multisystem vasculitis, late infection reaction, and mucocutaneous ulcerations in a mammal, said method comprising administering to said mammal a lactam derivative corresponding to formula I

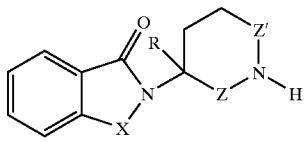

wherein

X is CH$_2$, S or Se;

R is a C$_{1-6}$-alkyl group or a benzyl group; and

Z and Z' are different and denote CH$_2$ or CO, or Z and Z' are both CO;

with the proviso that when X is CH$_2$, R is not CH$_3$, or Z and Z' are not both CO, in racemic or in optically active form in an amount effective to attenuate cytokine release without eliminating immunocompetence.

2. A method according to claim 1, wherein R represents a C$_{1-3}$-alkyl group.

3. A lactam derivative corresponding to formula I

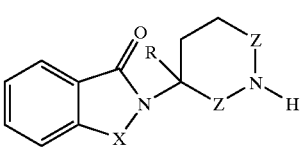

wherein

X is CH$_2$, S or Se;

R is a C$_{1-6}$-alkyl group or a benzyl group; and

Z and Z' are different and denote CH$_2$ or CO, or Z and Z' are both CO;

with the proviso that X is not S, when Z is CO and Z' is CH$_2$ and that X is not CH$_2$ when Z and Z' are both CO in racemic or optically active form.

4. A lactam derivative according to claim 3, wherein R is a C$_{1-3}$-alkyl group.

5. A process for preparing a lactam derivative corresponding to formula I

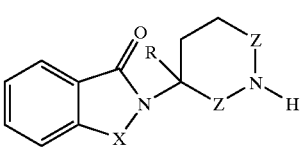

wherein

X is CH$_2$;

R is a C$_{1-6}$-alkyl group or a benzyl group; and

Z and Z' are different and denote CH$_2$ or CO, or Z and Z' are both CO, said process comprising reducing a compound of formula II

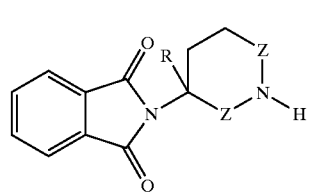

with zinc, lithium aluminum hydride or a complex borohydride in a solvent at a temperature in the range from +20° C. to +100° C.

6. A method of treating a condition involving excessive formation of cytokines in a mammal, said method comprising administering to said mammal a lactam derivative corresponding to formula I

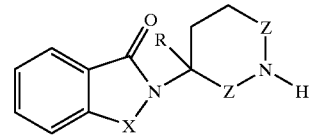

wherein

X is S or Se;

R is a C$_{1-6}$-alkyl group or a benzyl group; and

Z and Z' are different and denote CH$_2$ or CO, or Z and Z' are both CO;

in racemic or in optically active form in an amount effective to attenuate cytokine release without eliminating immunocompetence.

7. A method according to claim 6, wherein R represents a C$_{1-3}$-alkyl group.

8. A method according to claim 6, wherein said condition is selected from the group consisting of Graft-versus-Host-Syndrome, transplant or graft rejection, Morbus Behcet, erythema nodosum leprosum, Morbus Boeck, rheumatoid fever, rheumatoid arthritis, lupus erythematodes, stomatitis aphthosa, autoimmune consequences of chronic infections, Morbus Crohn, multisystem vasculitis, late infection reaction, and mucocutaneous ulcerations.

9. A method of inhibiting neoangiogenesis in a mammal comprising administering to said mammal an effective neoangiogenesis inhibiting amount of a lactam derivative corresponding to the formula I

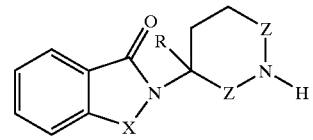

wherein

X is S or Se;

R is a C$_{1-6}$-alkyl group or a benzyl group; and

Z and Z' are different and denote CH$_2$ or CO, or Z and Z' are both CO;

in racemic or in optically active form.

10. A lactam derivative corresponding to formula I

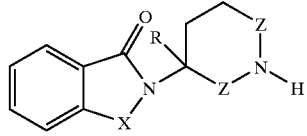

wherein
X is S or Se;
R is a $C_{1-6}$-alkyl group or a benzyl group; and
Z and Z' are different and denote $CH_2$ or CO, or Z and Z' are both CO;
with the proviso that X is not S, when Z is CO and Z' is $CH_2$ in racemic or optically active form.

11. A lactam derivative according to claim 10, wherein R is a $C_{1-3}$-alkyl group.

12. A method of treating a condition selected from the group consisting of Graft-versus-Host-Syndrome, erythema nodosum leprosum and stomatitis aphthosa, with the proviso that Graft-versus-Host-Syndrome does not include corneal graft rejection, in a mammal, said method comprising administering to said mammal a lactam derivative corresponding to formula I

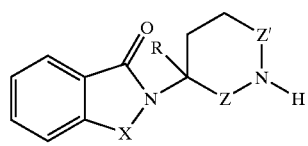

wherein
X is $CH_2$, S or Se;
R is a $C_{1-6}$-alkyl group or a benzyl group; and
Z and Z' are different and denote $CH_2$ or CO, or Z and Z' are both CO;
in racemic or in optically active form in an amount effective to attenuate cytokine release without eliminating immunocompetence.

13. A method according to claim 12, wherein R represents a $C_{1-3}$ alkyl group.

* * * * *